(12) United States Patent
Pinsonneault et al.

(10) Patent No.: US 8,060,379 B1
(45) Date of Patent: Nov. 15, 2011

(54) SYSTEMS AND METHODS FOR ALTERNATE PRICING FOR PRESCRIPTION DRUGS

(75) Inventors: Roger Pinsonneault, Alpharetta, GA (US); James Morgan Ringold, Lawrenceville, GA (US)

(73) Assignee: McKesson Financial Holdings Limited, Hamilton (BM)

( * ) Notice: Subject to any disclaimer, the term of this patent is extended or adjusted under 35 U.S.C. 154(b) by 603 days.

(21) Appl. No.: 12/101,997

(22) Filed: Apr. 13, 2008

(51) Int. Cl.
*G06Q 50/00* (2006.01)
*G06Q 40/00* (2006.01)

(52) U.S. Cl. ............................................. 705/2; 705/4

(58) Field of Classification Search .................... 705/2–4
See application file for complete search history.

(56) References Cited

U.S. PATENT DOCUMENTS

| | | | |
|---|---|---|---|
| 5,550,734 A | 8/1996 | Tarter et al. | |
| 5,628,530 A | 5/1997 | Thornton | |
| 6,012,035 A | 1/2000 | Freeman et al. | |
| 6,757,898 B1 | 6/2004 | Ilsen et al. | |
| 6,769,228 B1 | 8/2004 | Mahar | |
| 7,155,397 B2 | 12/2006 | Alexander et al. | |
| 2002/0002495 A1 | 1/2002 | Ullman | |
| 2002/0087583 A1 | 7/2002 | Morgan et al. | |
| 2002/0095314 A1* | 7/2002 | Bodsworth et al. | 705/2 |
| 2002/0111832 A1 | 8/2002 | Judge | |
| 2002/0198831 A1 | 12/2002 | Patricelli et al. | |
| 2003/0009367 A1 | 1/2003 | Morrison | |
| 2003/0050799 A1 | 3/2003 | Jay et al. | |
| 2003/0149625 A1 | 8/2003 | Leonardi et al. | |
| 2003/0154163 A1 | 8/2003 | Phillips et al. | |
| 2003/0229540 A1 | 12/2003 | Algiene | |
| 2004/0039599 A1 | 2/2004 | Fralic | |
| 2004/0059600 A1* | 3/2004 | Ball et al. | 705/2 |
| 2004/0073457 A1 | 4/2004 | Kalies | |

(Continued)

FOREIGN PATENT DOCUMENTS

CA 2482370 3/2006

(Continued)

OTHER PUBLICATIONS

Abrams, Lawrence W. "Pharmacy Benefit Managers As Bargaining Agents", Paper presented at the Western Economic Association International, 80th Annual Conference Jul. 6, 2005 San Francisco, the Dec. 10, 2005 entry accessed at http://web.archive.org/web/20051219093448/http://www.nu-retail.com/pbm_bargaining_paper.pdf on Aug. 23, 2011.*

(Continued)

*Primary Examiner* — Robert Morgan
*Assistant Examiner* — Robert Sorey
(74) *Attorney, Agent, or Firm* — Sutherland Asbill & Brennan LLP

(57) ABSTRACT

Systems and methods may be provided for alternate pricing. The systems and methods may include receiving first information associated with a first claim transaction, where the first information identifies a first drug, a first quantity of the first drug, and a first price for the first drug, determining a first product classification for the identified first drug, where the first product classification indicates that the identified first drug is a preferred drug, and updating an alternate pricing database with the first price for the first drug. The systems and methods may also include utilizing the alternate database to identify one or more lower-cost alternate drugs that are therapeutic alternatives for a requested drug. Customers may be provided with information regarding the identified lower-cost alternate drugs.

20 Claims, 9 Drawing Sheets

U.S. PATENT DOCUMENTS

| | | |
|---|---|---|
| 2004/0078234 A1 | 4/2004 | Tallal, Jr. |
| 2004/0117323 A1 | 6/2004 | Mindala |
| 2004/0139008 A1 | 7/2004 | Mascavage, III |
| 2004/0148198 A1 | 7/2004 | Kalies |
| 2004/0249745 A1 | 12/2004 | Baaren |
| 2005/0015280 A1 | 1/2005 | Gabel et al. |
| 2005/0060201 A1 | 3/2005 | Connely et al. |
| 2005/0102169 A1 | 5/2005 | Wilson |
| 2005/0154627 A1 | 7/2005 | Zuzek et al. |
| 2005/0187793 A1 | 8/2005 | Myles |
| 2005/0197862 A1 | 9/2005 | Paterson et al. |
| 2005/0240473 A1 | 10/2005 | Ayers |
| 2005/0288972 A1 | 12/2005 | Marvin et al. |
| 2006/0020514 A1 | 1/2006 | Yered |
| 2006/0026041 A1 | 2/2006 | Ullman et al. |
| 2006/0036470 A1* | 2/2006 | Oaks ............................. 705/2 |
| 2006/0149595 A1* | 7/2006 | Williams et al. ............... 705/2 |
| 2006/0149784 A1 | 7/2006 | Tholl et al. |
| 2006/0184391 A1 | 8/2006 | Barre et al. |
| 2006/0206425 A1 | 9/2006 | Sharma |
| 2006/0212318 A1* | 9/2006 | Dooley et al. ................ 705/4 |
| 2006/0259363 A1 | 11/2006 | Jhetam |
| 2007/0005402 A1 | 1/2007 | Kennedy et al. |
| 2007/0050209 A1 | 3/2007 | Yered |
| 2007/0136100 A1 | 6/2007 | Daugherty et al. |
| 2007/0192206 A1* | 8/2007 | Manesh et al. ................ 705/26 |
| 2007/0203750 A1 | 8/2007 | Volcheck |
| 2007/0226009 A1* | 9/2007 | Hicks ............................ 705/2 |
| 2007/0233525 A1 | 10/2007 | Boyle |
| 2007/0233526 A1 | 10/2007 | Hoffman et al. |
| 2007/0239493 A1 | 10/2007 | Sweetland et al. |
| 2007/0265887 A1 | 11/2007 | McLaughlin et al. |
| 2008/0183492 A1* | 7/2008 | Warren et al. ................. 705/2 |
| 2009/0048864 A1* | 2/2009 | Kozlowski et al. ............ 705/2 |
| 2009/0210286 A1* | 8/2009 | Bisdikian ...................... 705/10 |

FOREIGN PATENT DOCUMENTS

| | | |
|---|---|---|
| WO | 9503569 | 2/1995 |
| WO | 0039737 | 7/2000 |
| WO | 2007025295 | 3/2007 |

OTHER PUBLICATIONS

Sampson, R.J., Taking Control of Health Care Costs, Best's Review—Life Health Insurance Edition, Nov. 1983, pp. 64-66, vol. 84, Issue 7, USA.

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic: On-line Goes In-House, Chain Store Age Executive, Jan. 1987, pp. 128-132. vol. 63, Issue 1, USA.

Anonymous, TechRx Announces Successful Beta Deployment of T-Rex. PR Newswire. May 13, 2002.

Non-Final Office Action mailed Aug. 4, 2010 for U.S. Appl. No. 12/143,548 (23 pages).

Non-Final Office Action mailed Aug. 4, 2010 for U.S. Appl. No. 12/143,548.

Final Office Action for U.S. Appl. No. 12/143,548 mailed Jan. 19, 2011.

* cited by examiner

SYSTEMS AND METHODS FOR ALTERNATE PRICING FOR PRESCRIPTION DRUGS

FIELD OF THE INVENTION

Aspects of the invention relate generally to prescription drugs, and more particularly, to systems and methods for capturing and providing alternate pricing for prescription drugs.

BACKGROUND OF THE INVENTION

With the increasing cost of prescription drugs, patients have become a very price-sensitive group. Indeed, a patient's out-of-pocket cost for a drug may influence the extent to which a patient fills or refills a prescription or otherwise chooses another lower-cost drug. However, alternate pricing information for comparable drugs is typically not readily known to patients, pharmacists, and/or physicians. Accordingly, there is a need in the industry for systems and methods for capturing and providing alternate pricing for drugs.

SUMMARY OF THE INVENTION

Example embodiments of the invention may provide for systems and methods for capturing and providing alternate pricing for drugs with a variety of marketplaces, including, but not limited to, the 100% co-pay (e.g., discount programs), cash, and funded (e.g., insurance plans or other third-party payors) transaction marketplace.

According to an example embodiment of the invention, there is a method for alternate pricing. The method may include receiving first information associated with a first claim transaction, where the first information identifies a first drug, a first quantity of the first drug, and a first price for the first drug, determining a first product classification for the identified first drug, where the first product classification indicates that the identified first drug is a preferred drug, and updating an alternate pricing database with the first price for the first drug.

According to another example embodiment of the invention, there may be a system. The system may include a switch provider that interconnects a pharmacy and a payor, where the switch provider is operative to route a first claim transaction between the pharmacy and the payor, and an alternate pricing qualification module in communication with the switch provider, wherein the alternate pricing qualification module may be operative to receive, from the switch provider, first information associated with the first claim transaction, where the first information identifies a first drug, a first quantity of the first drug, and a first price for the first drug, determine a first product classification for the identified first drug, where the first product classification indicates that the identified first drug is a preferred drug, and update an alternate pricing database with the first price for the first drug.

According to yet another example embodiment of the invention, there may be a method for alternate pricing. The method may include receiving information associated with a claim request, wherein the received information includes an identification of a requested drug and a price for the requested drug, identifying one or more alternate drugs for the requested drug, where the one or more alternate drugs are therapeutic alternates to the requested drug, determining that at least one of the identified alternate drugs is at a lower cost than the requested drug, and transmitting a message with an indication of availability of at least one alternate drug and pricing information associated with the at least one alternate drug.

BRIEF DESCRIPTION OF THE DRAWINGS

Reference will now be made to the accompanying drawings, which are not necessarily drawn to scale, and wherein.

DETAILED DESCRIPTION

Figure 1:
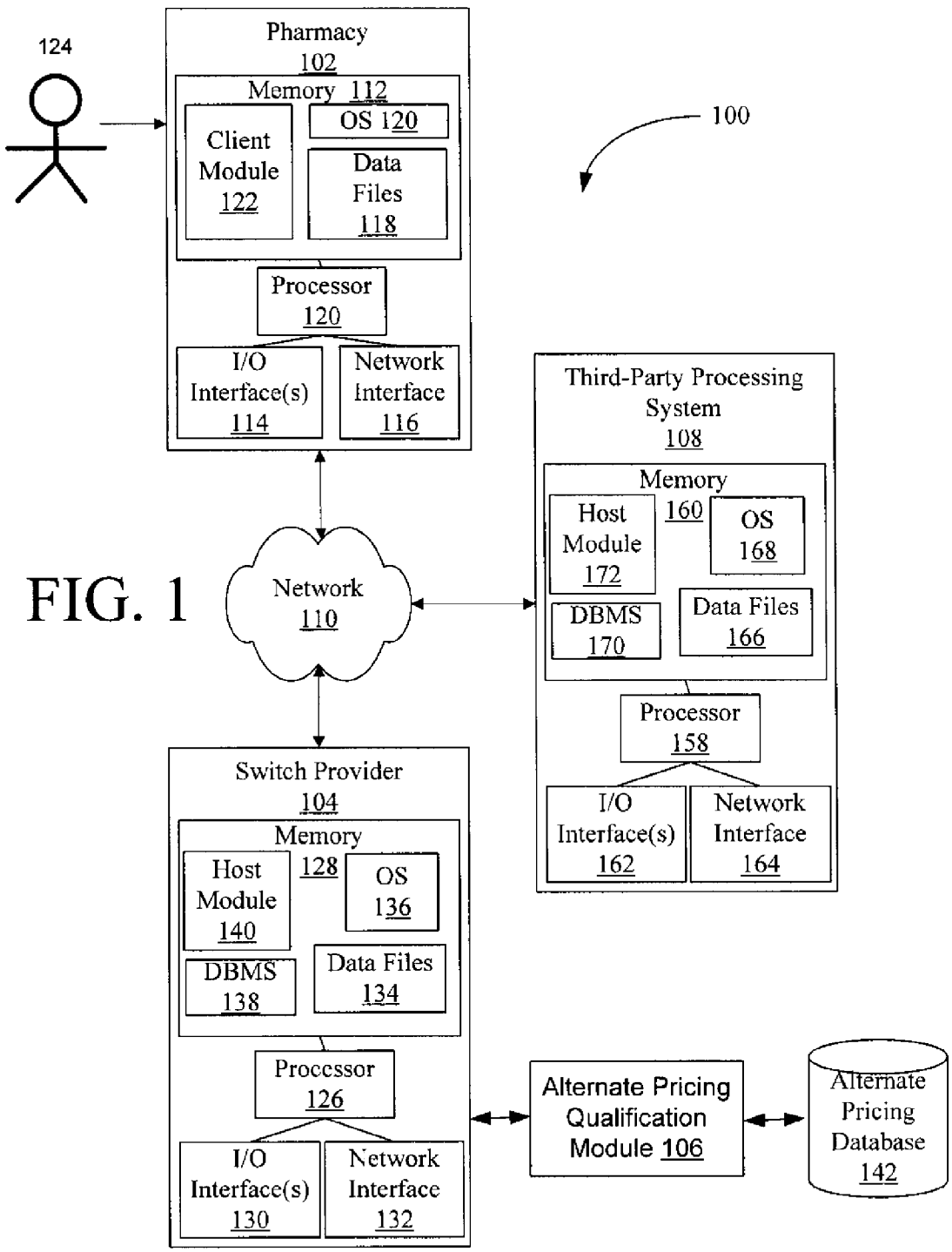
FIG. 1 shows a block diagram of a system for dynamically capturing, and providing, alternate pricing information for therapeutic alternates, according to an example embodiment of the invention.

Example embodiments of invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

The invention is described below with reference to block diagrams and flowchart illustrations of systems, methods, apparatuses and computer program products according to embodiments of the invention. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer such as a switch, or other programmable data processing apparatus to produce a machine, such that the instructions which execute on the computer or other programmable data processing apparatus create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means that implement the function specified in the flowchart block or blocks. The computer program instructions may also be loaded onto a computer or other programmable data processing apparatus to cause a series of operational elements or steps to be performed on the computer or other programmable apparatus to produce a computer implemented process such that the instructions that execute on the computer or other programmable apparatus provide elements or steps for implementing the functions specified in the flowchart block or blocks.

Accordingly, blocks of the block diagrams and flowchart illustrations support combinations of means for performing the specified functions, combinations of elements or steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions, elements or steps, or combinations of special purpose hardware and computer instructions.

The terms "alternate drug," "therapeutic alternative," "therapeutic equivalent," "therapeutic equivalent drug," "therapeutically equivalent drug," and "therapeutically equivalent item" are used interchangeably throughout the description, and should be construed to cover any drug, medication, or chemical composition having the same effects, similar effects, or substantially similar therapeutic effects on a person, patient, or consumer as a prescribed drug, medication, or chemical composition when taken in an appropriate dosage. Indeed, therapeutic alternates can oftentimes be used to treat the same diseases or ailments.

In accordance with example embodiments of the invention, a consumer may be provided with certain pricing information in order to provide the consumer with an opportunity to select a lower-cost therapeutic alternate. Indeed, the consumer ordering, requesting, or otherwise considering a particular drug may be presented with information regarding other therapeutic alternates that may meet the consumer's health requirements. If there are other therapeutic alternates that will meet the consumer's health requirements, then the consumer may also be presented with information specifying which, and/or the extent to which, those other therapeutic alternates will decrease the consumer's medication costs.

An example system in accordance with an embodiment of the invention is shown in FIG. 1. FIG. 1 shows a block diagram of a system 100 for dynamically capturing, and providing, alternate pricing information for therapeutic alternates. In particular, the system 100 of FIG. 1 may include at least one pharmacy 102, at least one switch provider 104, and at least one third-party processing system 108, which are each configured for accessing and reading associated computer-readable media having stored thereon data and/or computer-executable instructions for implementing the various methods of the invention. Generally, network devices and systems, including the one or more pharmacies 102, switch providers 104, and third-party processing system 108 have hardware and/or software for transmitting and receiving data and/or computer-executable instructions over a communications link and a memory for storing data and/or computer-executable instructions. These network devices and systems may also include a processor for processing data and executing computer-executable instructions, as well as other internal and peripheral components that are well known in the art. As used herein, the term "computer-readable medium" describes any form of memory or a propagated signal transmission medium. Propagated signals representing data and computer-executable instructions are transferred between network devices and systems.

As shown in FIG. 1, a pharmacy 102, switch provider 104, and third-party processing system 108 may be in direct communication with each other or via a network 110, which as described below can include one or more private and public networks, including the Internet. Each of these components—the pharmacy 102, the switch provider 104, the third-party processing system 108, and the network 110—will now be discussed in turn. First, the pharmacy 102 may be any processor-driven device, such as a personal computer, laptop computer, handheld computer, and the like. In addition to having a processor 120, the pharmacy 102 may further include a memory 112, input/output ("I/O") interface(s) 114 and a network interface 116. The memory 112 may store data files 118 and various program modules, such as an operating system ("OS") 120 and a client module 122. The client module 122 may be an Internet browser or other software, including a dedicated program, for interacting with the switch provider 104. For example, a user 124, such as a consumer, pharmacist, or other pharmacy employee, may utilize the client module 122 in preparing and providing a prescription drug request or order to the switch provider 104 for processing. The pharmacy 102 may also utilize the client module 122 to retrieve or otherwise receive data from the switch provider 104, including alternate pricing information for one or more therapeutic alternates.

Still referring to the pharmacy 102, the I/O interface(s) 114 may facilitate communication between the processor 120 and various I/O devices, such as a keyboard, mouse, printer, microphone, speaker, monitor, bar code readers/scanners, RFID readers, and the like. The network interface 116 may take any of a number of forms, such as a network interface card, a modem, a wireless network card, and the like. These and other components of the pharmacy 102 will be apparent to those of ordinary skill in the art and are therefore not discussed in more detail herein.

The switch provider 104 may include any processor-driven device that is configured for receiving, processing, and fulfilling requests from the pharmacy 102 related to pharmacy, benefits, and/or discount transactions. The switch provider 104 may communicate with, or otherwise include, an alternate pricing qualification module 106, which may operate to store or retrieve alternate pricing information for therapeutic alternates from an alternate pricing database 142. The switch provider 104 may therefore include a processor 126, a memory 128, input/output ("I/O") interface(s) 130, and a network interface 132. The memory 128 may store data files 434 and various program modules, such as an operating system ("OS") 136, a database management system ("DBMS") 138, and the host module 140. The host module 140 receives, processes, and responds to requests from the respective client module 122 of pharmacy 102, and further receives, processes, and responds to requests from the respective host modules 172 of the third-party processing system 108. Likewise, where the alternate pricing qualification module 106 is provided separately from the switch provider 104, the host module 140 may transmit claim, drug, and or pricing information to the alternate pricing qualification module 106, and receive alternate pricing information from the alternate pricing qualification module 106.

According to an example embodiment of the invention, alternate pricing qualification module 106 may include computer-executable instructions for implementing the methods described herein. For example, the alternate pricing qualification module 106 may be operative to selectively determine which of the received claim, drug, and/or pricing information to store in the alternate pricing database 142. Likewise, the alternate pricing qualification module 106 may determine which, if any, alternate pricing information to provide from the alternate pricing database 142 in response to a requested drug.

The third-party processing system 108 may include any processor-driven device that is configured for receiving, processing, and fulfilling requests from the pharmacy 102 or switch provider 104 related to pharmacy, benefits, and/or discount transactions, including those associated with alternate pricing for therapeutic alternates. The third-party processing system 108 may include a processor 158, a memory 160, input/output ("I/O") interface(s) 162, and a network interface 164. The memory 160 may store data files 166 and various program modules, such as an operating system ("OS") 168, a database management system ("DBMS") 170, and a host module 172. The host module 172 receives, processes, and responds to requests from the client module 122 of pharmacy 102, and further receives, processes, and responds to requests from the host module 140 of the switch provider 104. Those of ordinary skill in the art will appreciate that the PBM 408 may include alternate and/or additional components, hardware or software.

The network 110 may include any telecommunication and/or data network, whether public, private, or a combination thereof, including a local area network, a wide area network, an intranet, an internet, the Internet, intermediate hand-held data transfer devices, and/or any combination thereof and may be wired and/or wireless. The network 110 may also allow for real-time, off-line, and/or batch transactions to be transmitted between the pharmacy 102 and the switch provider 104. Due to network connectivity, various methodologies as described herein may be practiced in the context of distributed computing environments. Although the pharmacy 102 is shown for simplicity as being in communication with the switch provider 104 via one intervening network 110, it is to be understood that any other network configuration is possible. For example, intervening network 110 may include a plurality of networks, each with devices such as gateways and routers for providing connectivity between or among networks 110. Instead of or in addition to a network 110, dedicated communication links may be used to connect the various devices in accordance with example embodiment invention. For example, the switch provider 104 may form the basis of network 110 that interconnects the pharmacy 102 and the third-party processing system 108.

Those of ordinary skill in the art will appreciate that the system 100 shown in and described with respect to FIG. 1 is provided by way of example only. Numerous other operating environments, system architectures, and device configurations are possible. Accordingly, embodiments of the invention should not be construed as being limited to any particular operating environment, system architecture, or device configuration.

Figure 2:
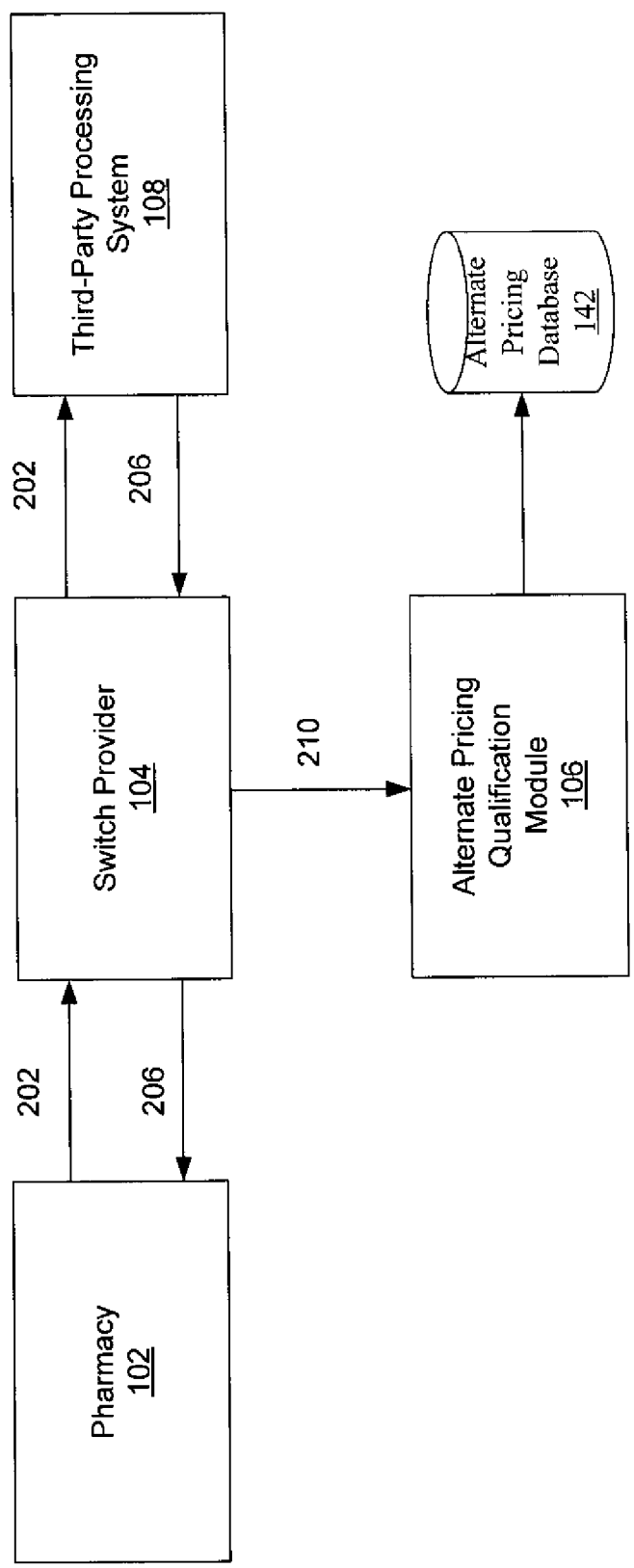
FIG. 2 illustrates an example block diagram for dynamic updates of an alternate pricing database, according to an example embodiment of the invention.
Figure 3:
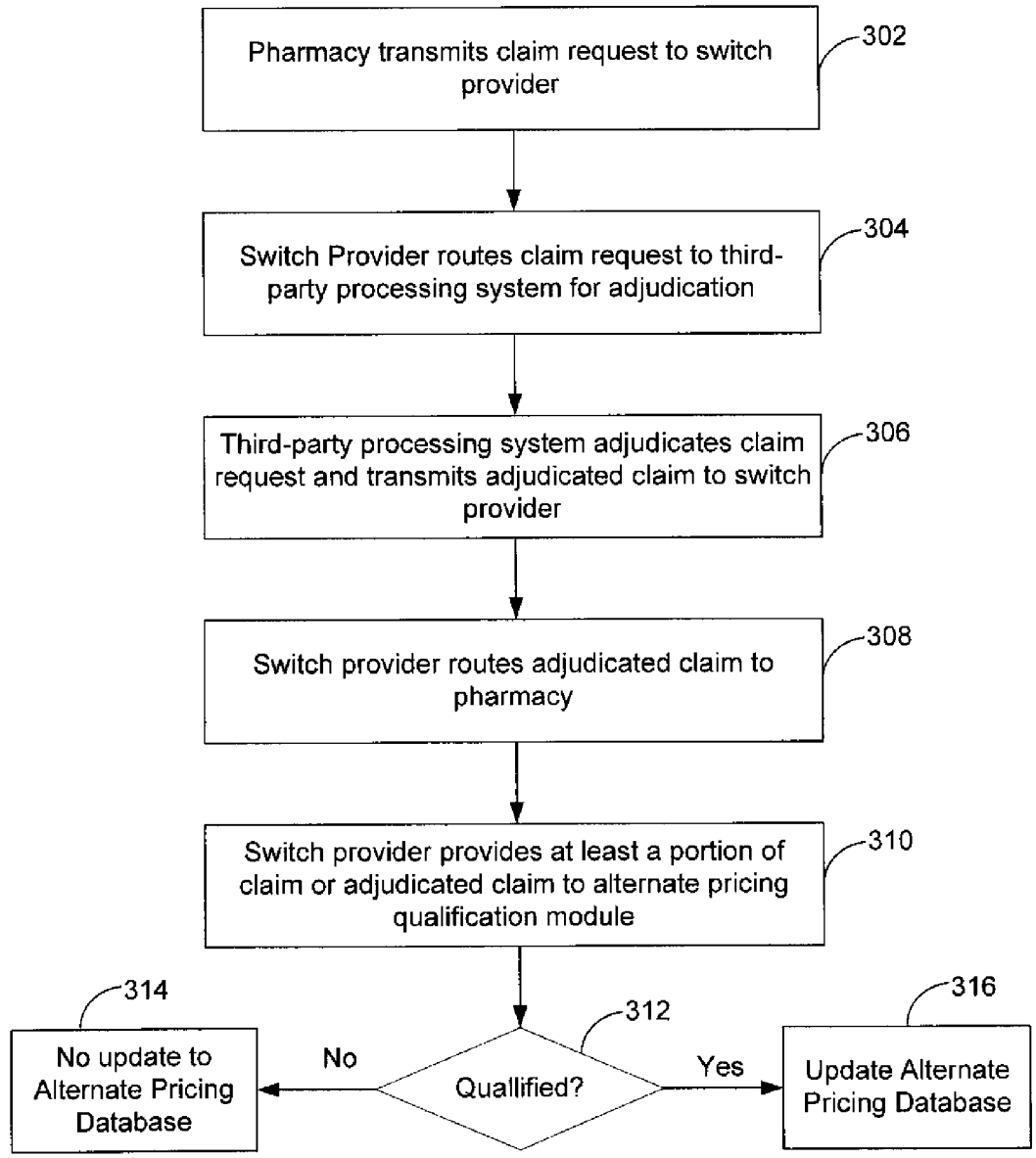
FIG. 3 illustrates an example flow diagram for dynamic updates of an alternate pricing database, according to an example embodiment of the invention.

FIG. 2 illustrates an example block diagram for dynamic updates of an alternate pricing database, according to an example embodiment of the invention. The block diagram of FIG. 2 will be discussed in conjunction with the flow diagram of FIG. 3. Referring now to FIGS. 2 and 3, in block 302, the pharmacy 102 transmits a claim request 202 on behalf of a customer to the switch provider 104. In an example embodiment of the invention, the claim request 202 may include one or more of the following information:
 an identification of the drug (e.g., National Drug Code (NDC)),
 a quantity of the drug,
 a price of the drug,
 the pharmacy's usual and customary (U&C) price charged for the drug (e.g., a cash customer cost),
 a date of the claim request, and
 a pharmacy identification number.

It will be appreciated that while some example information has been illustrated for the example claim request 202, it will be appreciated that alternate or additional information may also be included without departing from example embodiments of the invention. For example, the claim request 202 may also include a Banking Identification Number(BIN)/Processor Control Number (PCN) for identifying a third-party processing system 108 as a destination of the claim request 202.

In block 304, the switch provider 104 may receive the claim request 202, and route the claim request 202 to the third-party processing system 108 for further processing and/or adjudication. According to an example embodiment of the invention, the switch provider 104 may utilize the BIN/PCN in the received claim request 202 to determine which third-party processing system 108 to route the claim request 202 to. The switch provider 104 may also include a routing table, perhaps stored in memory 128, for determining which third-party payor 108 to route the claim request 202 to. According to an example embodiment of the invention, the third-party processing system 108 may be any pharmacy claims processing system such as a pharmacy benefits manager (e.g., a pharmacy benefits manager (PBM)), an insurance company, or a government payor (e.g., Medicare, Medicaid). Alternatively, the third-party processing system 108 may be a discount program processing system, including a discount program where a customer is responsible for paying for a portion or entire cost of the drug.

In block 306, the third-party processing system 108 receives and adjudicates the claim request 202. In particular, the third-party processing system 108 may determine benefits coverage for the received claim request 202 according to an adjudication process associated with eligibility, pricing, and/or utilization review. According to an example embodiment of the invention, the adjudication process may include determining a covered amount such as an insured amount, as well as a customer amount such as a co-pay amount. According to another example embodiment of the invention, the adjudication process may otherwise include determining a discounted price for a drug in accordance with a discount program. In block 306, the third-party processing system 108 transmits an adjudicated claim 206 to the switch provider 104. If the drug is covered, at least in part, by the third-party processing system 108, then the adjudicated claim 206 may include the covered amount, and the customer amount. Alternatively, the adjudicated claim may include the discounted price for a drug in accordance with a discount program. On the other hand, if the drug is not covered by the payor 108, then the adjudicated claim 206 may include a rejected claim notice indicating that the drug is not covered by the third-party processing system 108. The adjudicated claim 206 may also include some or all of the information included in the claim request 202, discussed herein.

In block 308, the switch provider 104 receives the adjudicated claim 206 from the third-party processing system 108. The switch 104 then routes the adjudicated claim 206 back to the pharmacy 102. At the pharmacy 102, the patient will then be responsible for any customer amount (e.g., co-pay amount) indicated by the adjudicated claim 206.

In block 310, the switch provider 104 may also provide some or all of the information in the claim request 202 or the adjudicated claim 206 to an alternate pricing qualification module 106 for further analysis. For example, the information provided to the alternate pricing qualification module 106 may include one or more of the following:

an identification of the drug (e.g., National Drug Code (NDC)), a quantity of the drug, a price of the drug, the pharmacy's usual and customary (U&C) price charged for the drug (e.g., a cash customer cost), a date of the claim request, a pharmacy identification number, and covered amount and/or customer amount.

In block 312, the alternate pricing qualification module 106 may qualify the received information to determine whether to store or update any pricing information for any therapeutic alternates in the alternate pricing database 142. As described herein, the alternate pricing qualification module 106 may examine the pharmacy identification number, the product classification, the quantity of the drug, and/or pricing information of the drug to determine whether to store or update any pricing information for therapeutic alternates in the alternate pricing database 142.

If the alternate pricing qualification module 106 determines that the received information does not qualify in block 312, then the alternate pricing qualification module 106 may proceed to block 314, where no updates are made to the alternate pricing database 142. On the other hand, if the alternate pricing qualification module 106 determines that the received information does qualify, then the alternate pricing database 142 will be updated in block 316.

It will be appreciated that variations of the flow diagram of FIG. 3 are available without departing from example embodiments of the invention. For example, the operation of the alternate pricing qualification module 106 may operate in tandem with the process for adjudicating the claim request by the third-party processing system 108. As an example, when the switch provider 104 routes the claim request 202 to the third-party processing system 304, the switch provider 104 could also route the claim request 202, or at least a portion thereof, to the alternate pricing qualification module 106 in accordance with blocks 310, 312, 314, and/or 316. In this scenario, the operation of the alternate pricing qualification module 106 may operate in tandem with the operation of the switch provider 104 and the third-party processing system 108. Indeed, the operation of blocks 310, 312, 314, and/or 316 may occur prior to blocks 304, 306, and for 308. For example, block 310 may occur between blocks 302 and 304, with blocks 312, 314, and 316 being performed in parallel with blocks 306 and/or 308.

Figure 4:
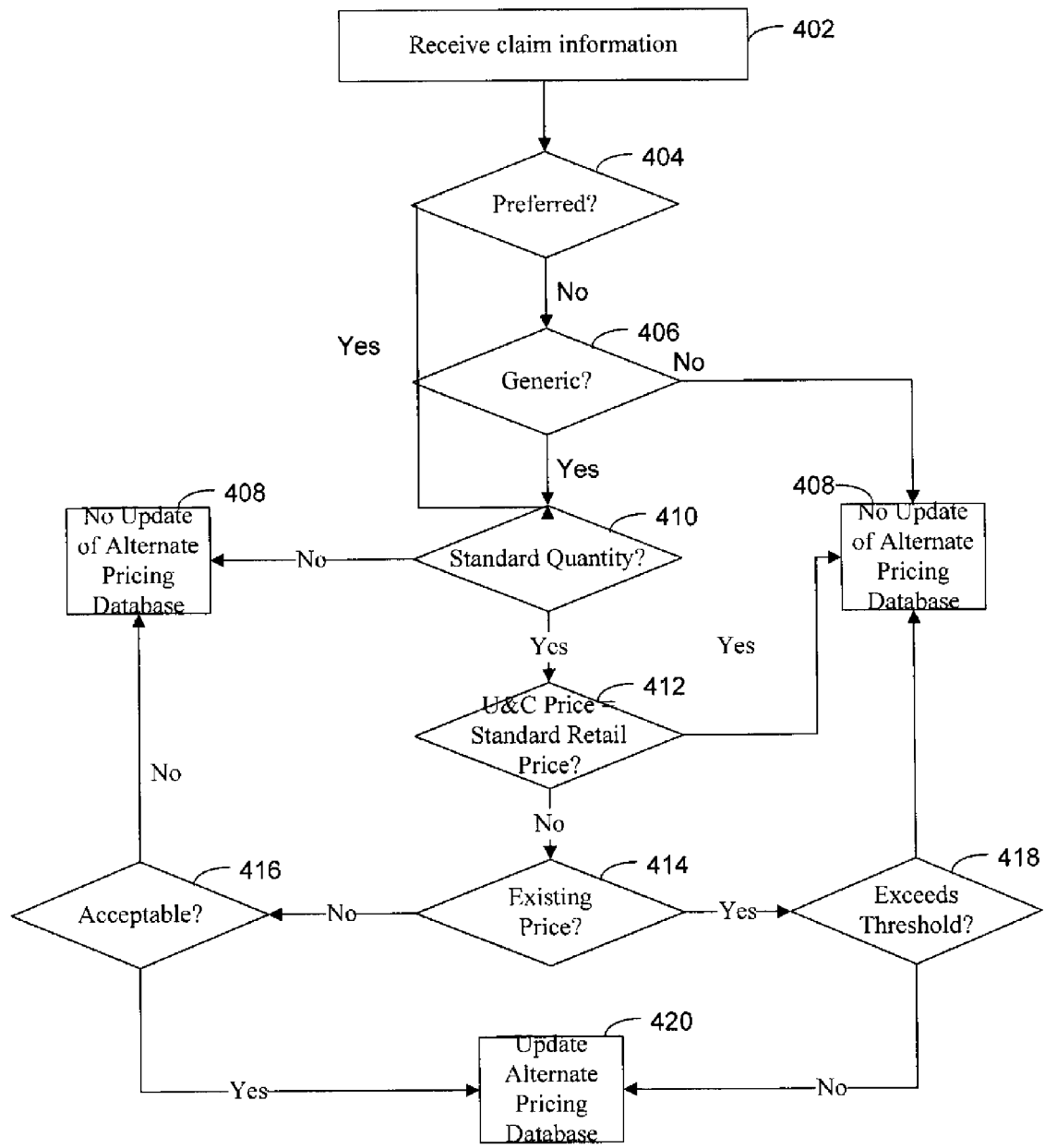
FIG. 4 illustrates an example flow diagram by which an alternate pricing qualification module may determine whether to update an alternate pricing database, according to an example embodiment of the invention.

FIG. 4 illustrates an example flow diagram by which an alternate pricing qualification module 106 may determine whether to update an alternate pricing database, according to an example embodiment of the invention. FIG. 4 begins in block 402 with the alternate pricing qualification module 106 receiving the claim information, which may include, but is not limited to, an identification of the drug, a quantity of the drug, a price of the drug, the pharmacy's usual and customary (U&C) price charged for the drug (e.g., a cash customer cost), a date of the claim request, and a pharmacy identification number.

In blocks 404 and 406, the alternate pricing qualification module 106 may determine a product classification of the identified drug. According to an example embodiment of the invention, the product classification may include the following: a preferred brand drug, a non-preferred brand drug, or a generic drug. Likewise, these product classifications for drugs may be pharmacy-specific, according to an example embodiment of the invention. Accordingly, the alternate pricing qualification module 106 may utilize the pharmacy identification number when determining a product classification for an identified drug. However, in other example embodiments of the invention, the product classifications may be determined by or associated with another entity, including a third-party processing system 108 such as a PBM.

Still referring to FIG. 4, a preferred brand drug may be identified in block 404 (e.g., Preferred?=Yes). For example, the preferred brand drug may be identified by the alternate pricing qualification module 106 determining that the identified drug (e.g., NDC) appears on a preferred brand list for a particular pharmacy 102. Similarly, a generic drug may be directly identified in block 406 (e.g., Generic?=Yes). For example, a generic drug may be identified by the alternate pricing qualification module 106 determining that the identified drug appears on a generic brand list for a particular pharmacy 102. Likewise, a non-preferred brand drug may be inferred using both blocks 404 and 406. For example, if the identified drug is neither a preferred brand drug in block 404 (e.g., Preferred?=No) nor a generic drug in block 406 (e.g., Generic?=No), then it may be inferred that the identified drug is a non-preferred brand drug.

If the alternate pricing qualification module 106 determines that the identified drug is a non-preferred brand drug (e.g., Preferred?=No and Generic?=No), then the alternate pricing qualification module 106 may not update the alternate pricing database 142, as illustrated in block 408. According to an example embodiment of the invention, an update may not be needed in the alternate pricing database 142 for a non-preferred brand drug since a non-preferred drug is typically at a higher price drug than a preferred brand drug or a generic drug. Indeed, according to an example embodiment of the invention, the alternate pricing qualification module 106 may not suggest a non-preferred brand in response to a requested drug. However, it will be appreciated that in alternate embodiments of the invention, it may be beneficial to update the alternate pricing database 142, as described herein, for non-preferred brand drugs as well to provide a more complete alternate pricing database 142. For example, the product classifications for drugs may change over time, as certain drugs are moved from non-preferred to preferred status, or vice versa.

On the other hand, if the alternate pricing qualification module 106 determines that the identified drug is a preferred brand drug (Preferred?=Yes) or a preferred generic drug (Generic?=Yes), then processing proceeds to block 410. Block 410 may determine whether the requested quantity of the identified drug is a standard quantity 410. In accordance with an example embodiment of the invention, the pricing information for drugs, including the preferred brand drugs and generic drugs as therapeutic alternates, may be stored for standard quantities. By selectively storing pricing information for standard quantities of drugs, the size and/or speed of the alternate pricing database 142 may be optimized. Accordingly, if claim information is received for a drug in a non-standard quantity, this claim information may not be utilized for updating the alternate pricing database 142, as illustrated in block 408. However, according to an alternative embodiment of the invention, the pricing information for various quantities of drugs may be stored in the alternate pricing database 402 as well.

Block 412 follows block 410 when there is a standard quantity of a requested drug present in the received claim information. In block 412, the alternate pricing qualification module 106 may determine whether the U&C price in the received claim information matches the pharmacy's standard retail price for the drug. If so, then there is no need to update the alternate pricing database 142, as illustrated in block 408, since the U&C price already reflects the price for the drug stored in the alternate pricing database 142. On the other hand, if the U&C price does not reflect the standard retail price in block 412, then processing proceeds to block 414.

In block 414, the alternate pricing qualification module 106 may determine whether there is an existing price for the drug in the alternate pricing database 142. If there is no existing price for the drug in the alternate pricing database 142, then processing may proceed to block 416. Block 416 may determine whether the price (e.g., U&C price) or other information provided in the received claim information is acceptable according to qualification rules. For example, the qualification rules may indicate that a received price is acceptable where it is within a certain amount or percentage from an established cost base, including an industry-established cost base. Examples of industry-established cost bases may include average wholesale prices (AWPs) or wholesale acquisition costs (WACs). It will be appreciated however that various cost bases may be utilized without departing from example embodiments of the invention. Other qualification rules may also be available without departing from example embodiments of the invention. For example, other qualification rules may specify that a received price is not fully acceptable until the same or substantially same price is likewise received for the same drug and/or quantity within a particular period of time.

If block 416 determines that the price is not acceptable for storage, then processing proceeds to block 408, where the alternate pricing database 142 is not updated. On the other hand, if block 416 determines that the price is acceptable for storage, then processing proceeds with the alternate pricing qualification module 106 directing storage of the received pricing information for the drug in the alternate pricing database 142, as illustrated in block 420.

Block 414 may also determine that a price for the drug already exists in the alternate database. If so, then processing may proceed to block 418. In block 418, the alternate pricing qualification module 106 may determine whether the received price for the drug exceeds one or more thresholds. For example, a threshold may be a certain amount or percentage from an established base cost, including an industry-established cost base. Examples of industry-established cost bases include an average wholesale price (AWP) or a wholesale acquisition cost (WAC) for the drug. Alternately, the threshold may be a certain amount or percentage from the previously stored price. The thresholds may also related to determining whether the same or substantially same price has been received for the same drug and/or quantity within a particular period of time.

If the received price does exceed one or more thresholds in block 418, then the alternate pricing database may not be updated, as illustrated in block 408. On the other hand, if the received price does not exceed one or more thresholds in block 418, then the alternate pricing qualification module 106 may direct storage of the updated pricing information for the drug in the alternate pricing database 142, as illustrated in block 420.

It will be appreciated that according to an example embodiment of the invention, the alternate pricing database 142 may receive and analyze claim information, perhaps as illustrated in FIG. 4, to maintain and update an alternate pricing database 142. Indeed, once the database scheme for the alternate pricing database 142 has been established for a particular pharmacy, claim transactions involving the pharmacy may be used by the alternate pricing qualification module 106 to dynamically update the pricing information of the alternate pricing database 142. As described herein, the dynamically updated alternate pricing database 142 may be used to suggest one or more lower cost therapeutic alternates, according to an example embodiment of the invention.

Table I below illustrates an example database records for an alternate pricing database 142, according to an example embodiment of the invention. As shown in Table I, the fields of the alternate pricing database 142 may include a therapeutic category, a product classification, a drug, one or more standard quantities, and a price. The therapeutic category field may indicate the condition or ailment being treated (e.g., allergies), or the therapeutic effects of the drug (e.g., antihyperlipidemic). Likewise, the therapeutic category may likewise be represented by, or otherwise correspond to, diagnosis codes or similar codes that may be provided as part of claim requests. It will be appreciated that the therapeutic category may be utilized to identify therapeutic alternates (e.g., one or more preferred brand drugs or generic drugs) for a requested drug.

TABLE I

| Therapeutic Category | Product Classification | Drug | Standard Quantity | Price |
|---|---|---|---|---|
| Category A | G (Generic) | Drug A-1 | 1 | $4 |
| Category A | P (Preferred) | Drug A-2 | 1 | $34.99 |
| Category A | NP (Non-preferred) | Drug A-3 | 1 | $49.99 |
| Category C | G (Generic) | Drug C-1 | 30 | $5 |
| Category C | P (Preferred) | Drug C-2 | 30 | $20 |
| Category C | P (Preferred) | Drug C-3 | 30 | $25 |
| Category C | NP (Non-preferred) | Drug C-4 | 30 | $45 |
| ... | ... | ... | ... | ... |

Still referring to Table I, the product classification field may include one or more tiers, including generic drugs, preferred brand drugs, non-preferred brand drugs, or yet other tiers. As described above with respect to FIG. 4, some alternate pricing databases 142 may not necessarily store drugs for all the product classifications described herein. For example, non-preferred brand drugs may be excluded if they are typically at a higher price than the generic drugs or preferred brand drugs. However, as also described herein, the non-preferred brand drugs could likewise be included as well. The drug field may identify the drug and/or dosage (e.g., XX mg tab Crestor). According to an example embodiment of the invention, the drug may alternately be represented using one or more codes, including the NDC associated with the drug. The standard quantity field may indicate the amount of the drug that is typically dispensed. It will be appreciated that there may be one or more standard quantities for any particular drug, where the standard quantities may relate to typical dispensing quantities. For example, a particular drug may have 14-day, 30-day, and 90-day standard quantities, according to an example embodiment of the invention. The price may indicate the usual and customary (U&C) price or similar price charged. According to an example embodiment of the invention, the alternate pricing database 142 may be comprised of separate databases or otherwise apportioned for each of the various pharmacies 102. For example, if there are two different pharmacies 102, then there may be two different version of Table I for each pharmacy 102. Indeed, each pharmacy 102 may specify the tiers or product classifications (e.g., generic, preferred, non-preferred etc.) for one or more drugs. Accordingly, claim information received or provided to each pharmacy 102 may be used to maintain and update the respective portions of the alternate pricing database 142. It will be appreciated that in alternate embodiments of the invention, the alternate pricing database 102, including the tiers or product classifications, may also be determined by or updated according to the preferences of the third-party processing system 108. For example, different version of Table I may be provided for each of a variety of third-party processing systems 108. In such a scenario, the third-party processing systems 108 may specify their respective product classifications for one or more drugs.

Figure 5:
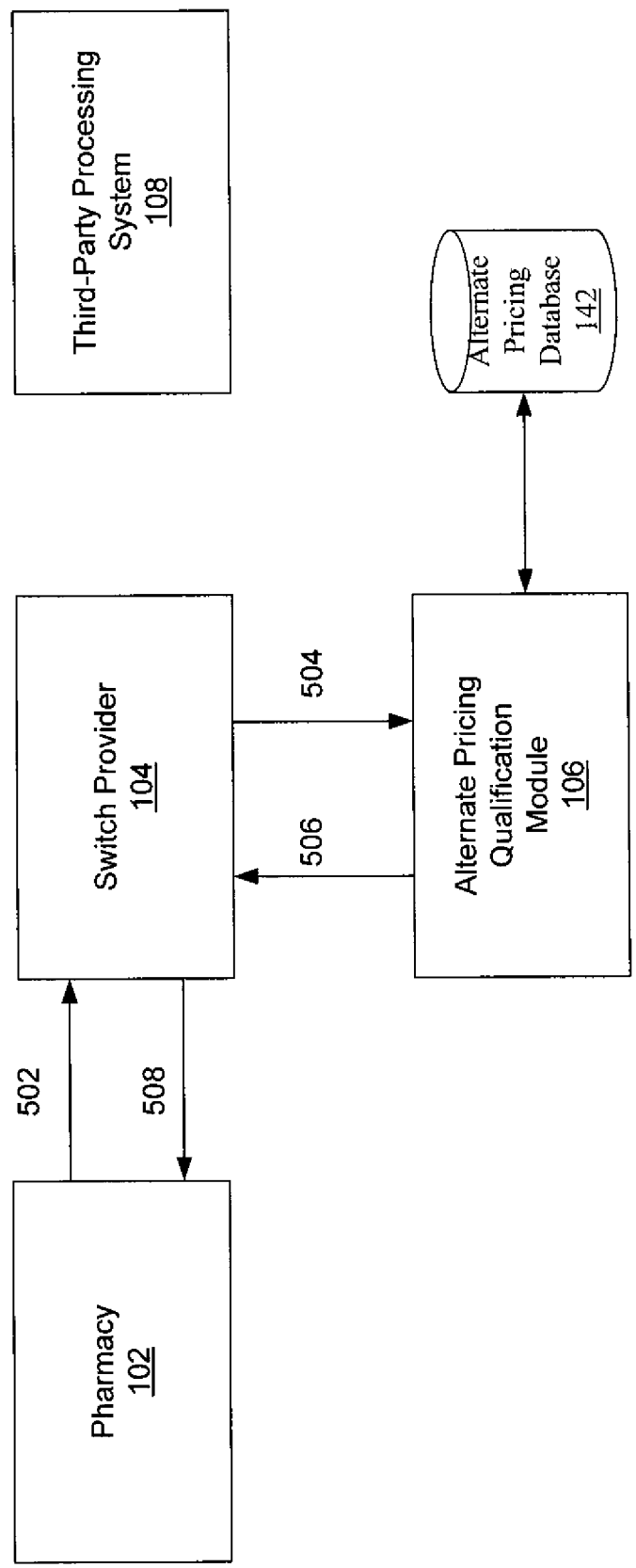
FIG. 5 illustrates an example block diagram of a system operation when a lower-cost therapeutic alternate is available, according to an example embodiment of the invention.

FIG. 5 illustrates an example block diagram of a system operation when a lower-cost therapeutic alternate is available, according to an example embodiment of the invention. The operation of the block diagram of FIG. 5 will be discussed in conjunction with the flow diagram of FIG. 6.

Figure 6:
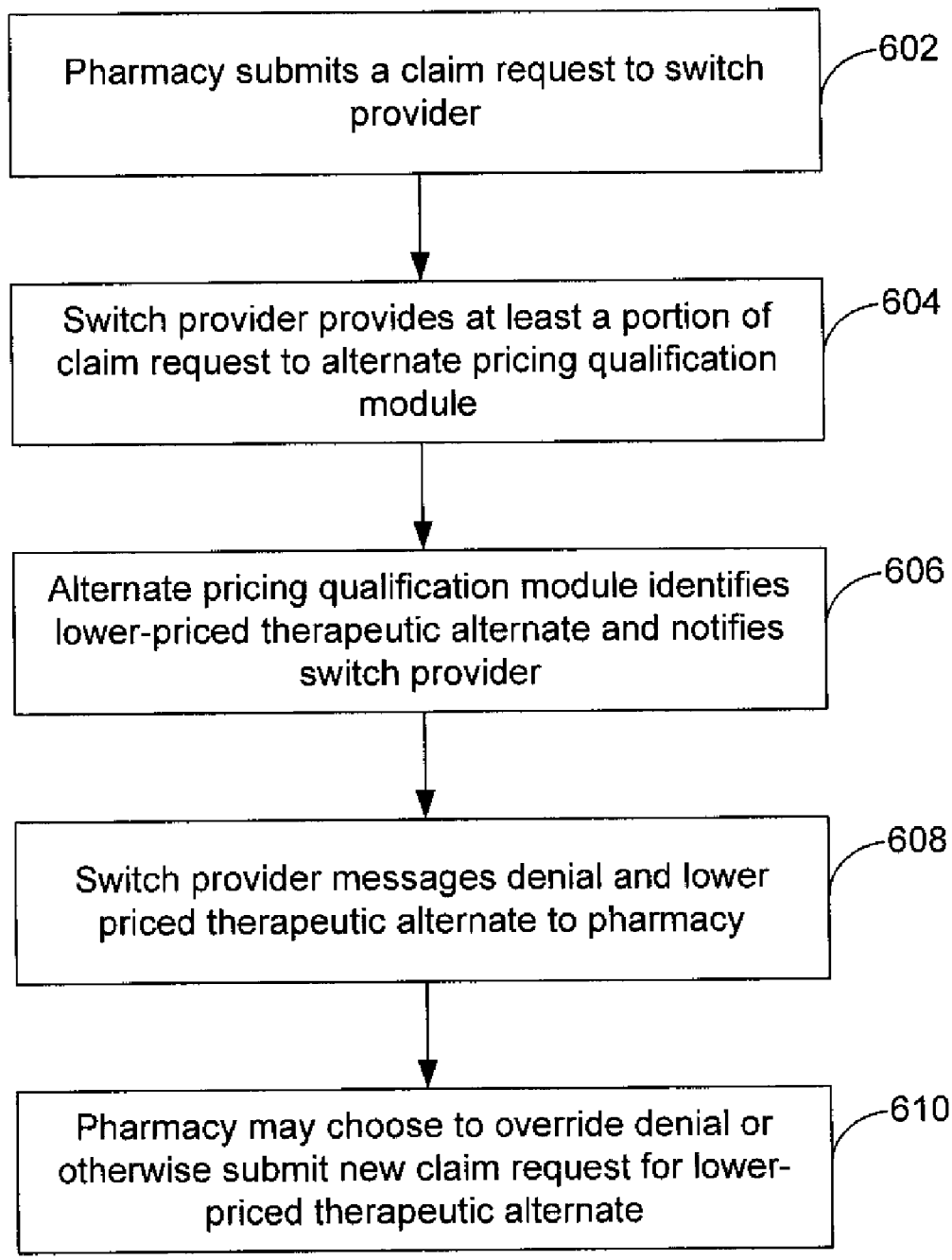
FIG. 6 illustrates an example flow diagram of a system operation when a lower-cost therapeutic alternate is available, according to an example embodiment of the invention.

Referring to FIGS. 5 and 6, in block 602, a pharmacy 102 may submit a claim request 502 to a switch provider 104. The switch provider 104 may then provide at least a portion of the claim request to the alternate pricing qualification module 106 to determine whether any lower-cost therapeutic alternates are available. According to an example embodiment of the invention, the communicated portion of the claim request may include an identification of the drug, a quantity of the drug, a price of the drug, and a pharmacy identification number. As will be described herein, the alternate pricing qualification module 106 may obtain pricing information for therapeutic alternates for the requested drug using alternate pricing database 142. For example, where the requested drug is a non-preferred brand drug, the alternate pricing qualification module 106 may identify one or more preferred brand drugs or generic drugs that are therapeutic alternates of the non-preferred brand drug. The alternate pricing qualification module 106 may then notify the switch provider 104 of the availability of lower-cost therapeutic alternates, as illustrated in block 606.

In block 608, the switch provider 104 may reject the received claim request 502, and instead, transmit a message 508 to pharmacy 102 with the denial. The message 508 may also include a message regarding the availability of lower-cost therapeutic alternates. For example, according to an example embodiment of the invention, the message may be as follows:

Message XX
Preferred Brand=$XX.XX/Quantity
Generic=$X.XX/Quantity
Override=ABCD

As shown by the message, above, one or more prices and quantities of the lower-cost therapeutic alternates, including a preferred brand drug or generic drug, may be identified in the message 508 to the pharmacy. Additionally, the message 508 may further include an override code. As shown in block 610, the pharmacy 102 may choose to resubmit the denied claim request 502 for the originally requested drug to the switch provider 104 using the supplied override code. Alternately, the pharmacy 102 may consult with the customer and/or customer's physician and submit a new claim request to the switch provider 104 using one of the lower-cost therapeutic alternates.

It will be appreciated that variations of FIGS. 5 and 6 are available in accordance with example embodiments of the invention. For example, the switch provider 104 may still route the received claim request to the third-party 108, and likewise, receive an adjudicated claim back from the third-party processing system 108. The adjudicated claim may then be routed back to the pharmacy 102 along with a message indicating that one or more lower-cost therapeutic alternates are available. To take advantage of the lower-cost therapeutic alternates are available, the pharmacy 104 may submit a claim reversal transaction to cancel the previously adjudicated claim, and resubmit a new claim for the lower-cost therapeutic alternate.

Figure 7:
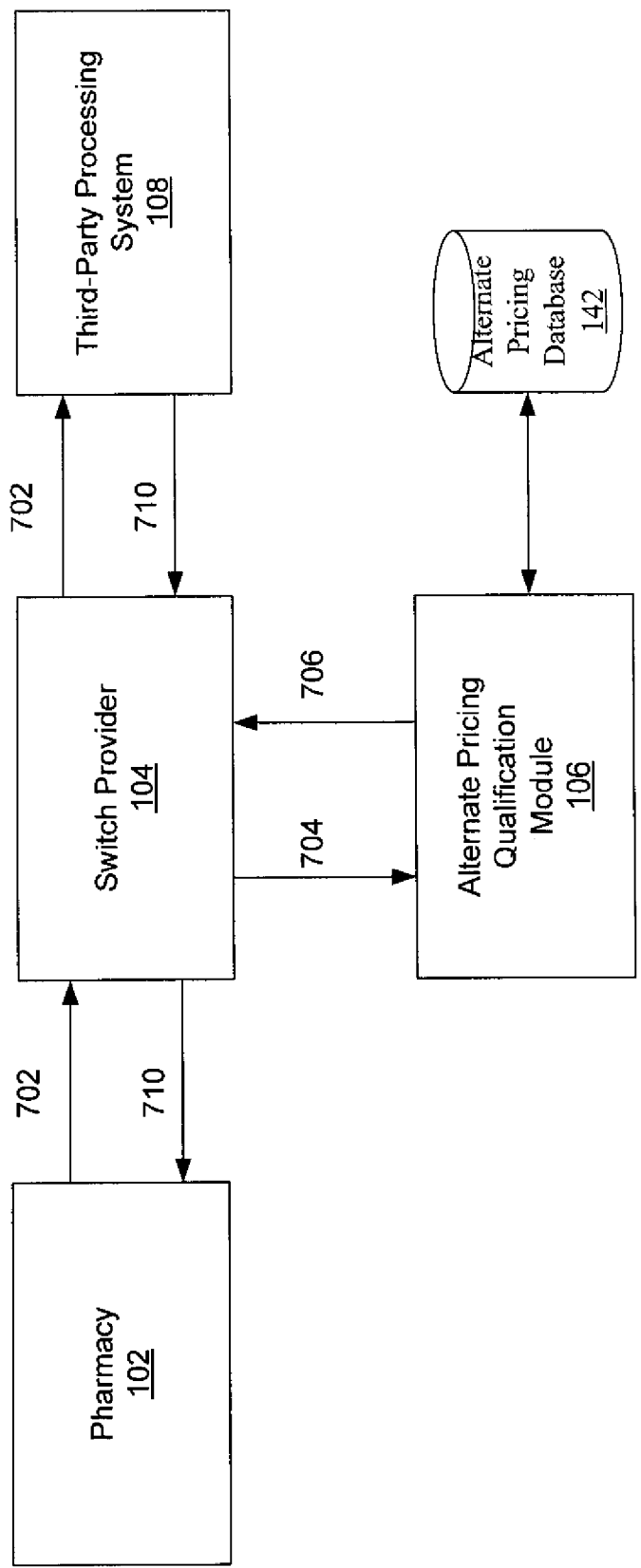
FIG. 7 illustrates an example block diagram of a system operation when no lower-cost therapeutic alternate is available, according to an example embodiment of the invention.

FIG. 7 illustrates an example block diagram of a system operation when no lower-cost therapeutic alternate is available, according to an example embodiment of the invention. The operation of the block diagram of FIG. 7 will be discussed in conjunction with the flow diagram of FIG. 8.

Figure 8:
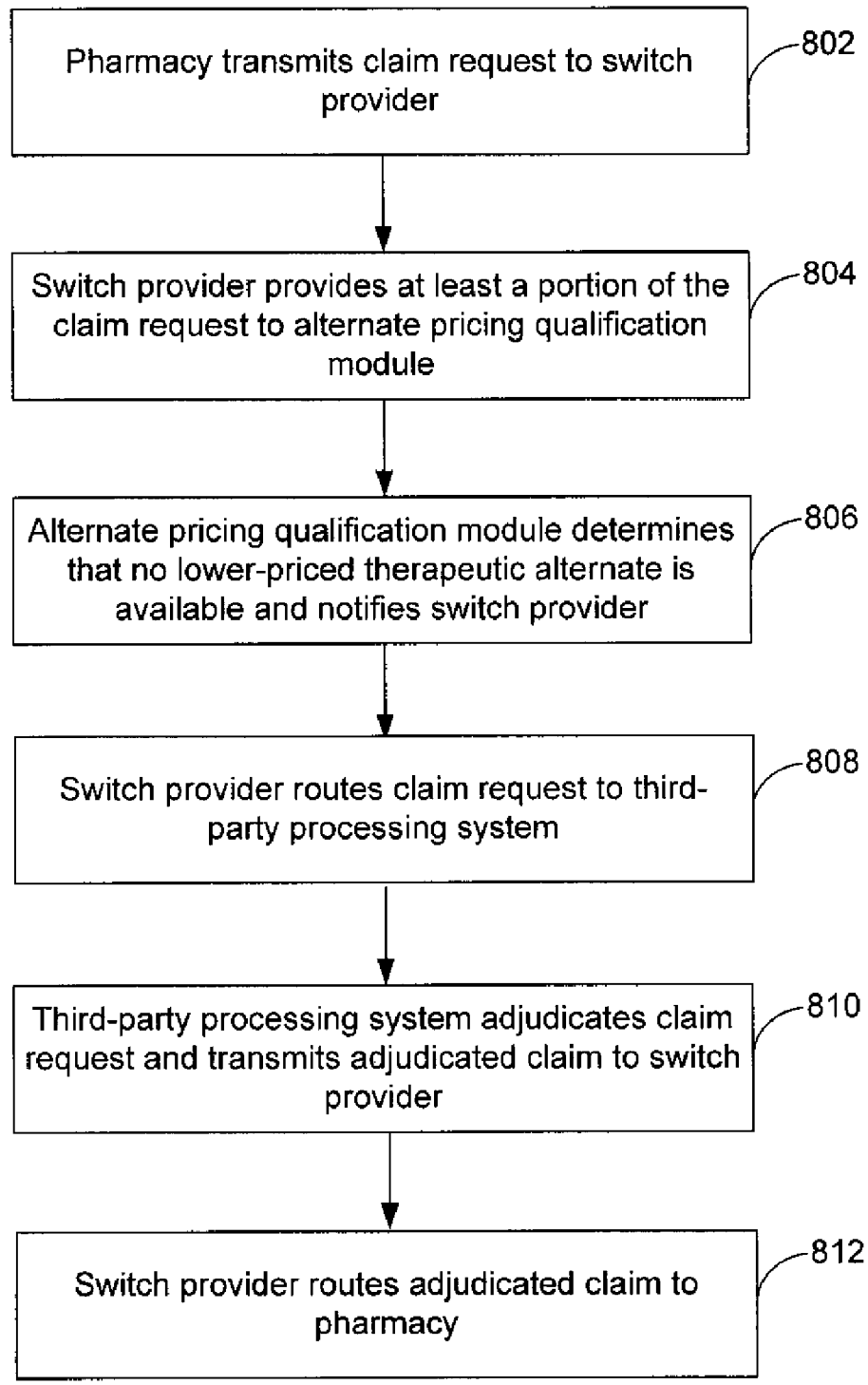
FIG. 8 illustrates an example flow diagram of a system operation when no lower-cost therapeutic alternate is available, according to an example embodiment of the invention.

Referring to FIGS. 7 and 8, in block 802, the pharmacy 102 transmits a claim request 702 to the switch provider 104. As described herein, the claim request 702 may include the following information: an identification of the drug, a quantity of the drug, a price of the drug, the pharmacy's usual and customary (U&C) price charged for the drug (e.g., a cash customer cost), a date of the claim request, and a pharmacy identification number. In block 804, the switch provider 104 may provide some or all of this claim request information in a query 704 to the alternate pricing qualification module 106. In block 806, the alternate pricing qualification module 106 may determine, based upon information in the alternate pricing database 142, that no lower-cost therapeutic alternate is available. In this case, the alternate pricing qualification module 106 may notify the switch provider 104 that no lower-cost therapeutic alternate is available.

In block 808, the switch provider 104 may route the claim 702 to the third-party processing system 108 for adjudication and/or benefits determination. In block 810, the third-party processing system 108 may determine the benefits coverage such as the covered amount and the customer amount, which may be provided as an adjudicated claim 710 to the switch provider 104. The switch provider 104 may then route the adjudicated claim 710 to the pharmacy 102, as illustrated in block 812. The pharmacy 102 may then dispense the requested drug to the customer.

Figure 9:
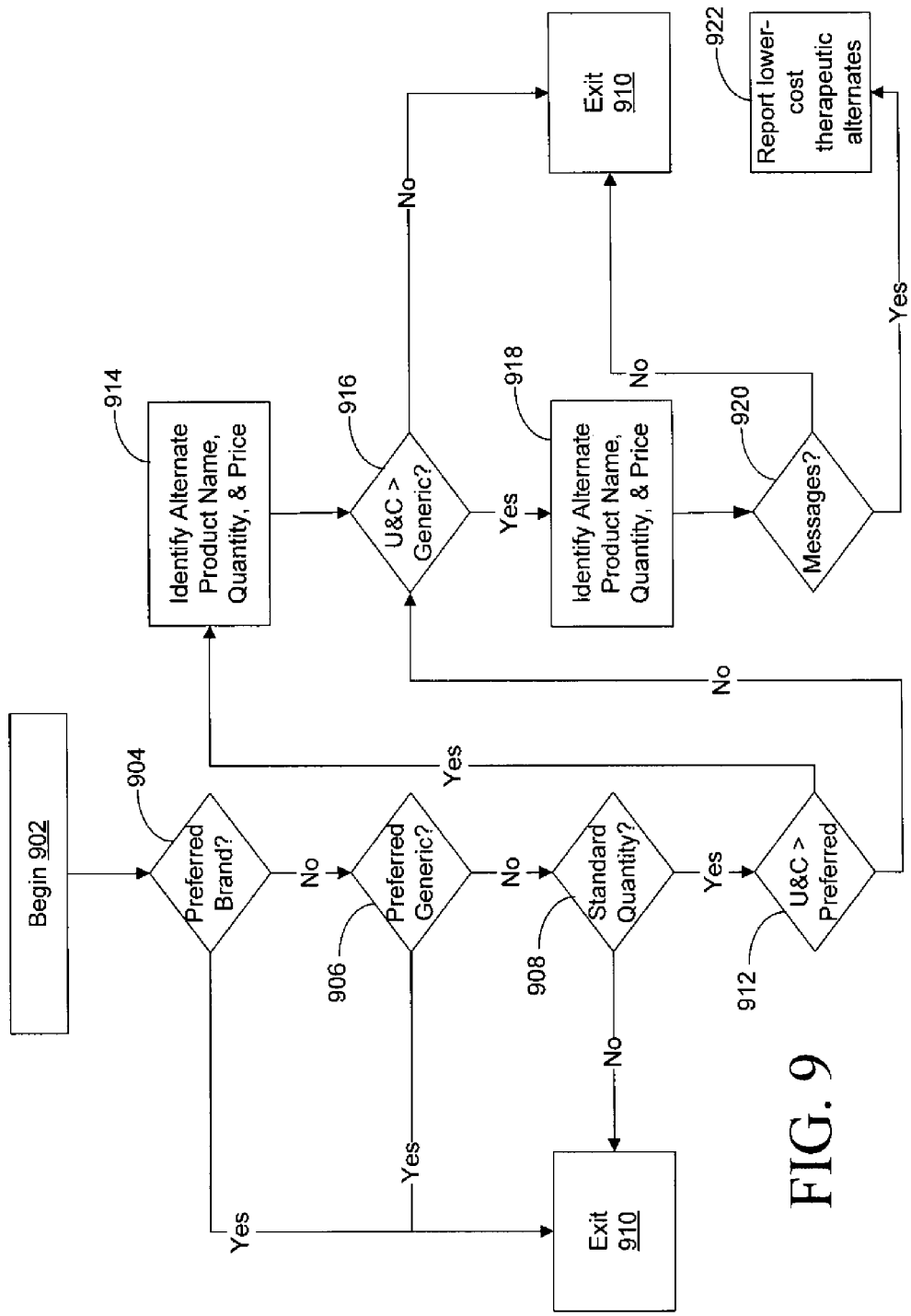
FIG. 9 illustrates an example flow diagram by which an alternate pricing qualification module 106 may determine whether one or more lower-cost therapeutic alternates are available according to an example embodiment of the invention.

FIG. 9 illustrates an example flow diagram by which an alternate pricing qualification module 106 may determine whether one or more lower-cost therapeutic alternates are available according to an example embodiment of the invention. As shown in FIG. 9, the process may begin in block 904 with the alternate pricing qualification module 106 receiving information associated with a claim request, such as an identification of the drug, a quantity of the drug, a price of the drug, the pharmacy's usual and customary (U&C) price charged for the drug, and a pharmacy identification number. In block 904, the alternate pricing qualification module 106 may examine the alternate pricing database 142 to determine whether the requested drug is a preferred brand drug. For example, the alternate pricing qualification module 106 may identify the portion of the alternate pricing database 142 that is associated with the pharmacy 102 to determine if the requested drug is listed as a preferred brand drug for that pharmacy 102. If the requested drug is already a preferred brand drug, then the alternate pricing qualification module 106 may exit, and the switch provider 104 may optionally be notified that no lower-cost therapeutic alternate is available, as illustrated in block 910. On the other hand, if the requested drug is not a preferred brand drug, then processing may proceed to block 906.

In block 906, the alternate pricing qualification module 106 may examine the alternate pricing database 142 to determine whether the requested drug is a preferred generic drug. For example, the alternate pricing qualification module 106 may identify the portion of the alternate pricing database 142 that is associated with the pharmacy 102 to determine if the requested drug is listed as a preferred generic drug for that pharmacy 102. If the requested drug is a preferred generic drug, then the alternate pricing qualification module 106 may exit, and the switch provider 104 may optionally be notified that no lower-cost therapeutic alternate is available, as illustrated in block 910.

If the requested drug is a non-preferred drug (e.g., Preferred Brand?=No, and Preferred Generic?=No), then processing may proceed to block 908 determining whether the requested drug quantity is a standard quantity. If the requested drug is not a standard quantity in block 908, the alternate pricing qualification module 106 may exit, and the switch provider 104 may optionally be notified that no lower-cost therapeutic alternate is available, as illustrated in block 910. On the other hand, if the requested drug quantity is a standard quantity, then processing proceeds with block 912 determining whether the U&C price exceeds the preferred drug price for the preferred drug identified as the therapeutic alternate in the alternate pricing database 142. For example, in block 912, the preferred drug that is a therapeutic alternate may be identified by matching the therapeutic category of the requested drug with the therapeutic category of the preferred drug in the alternate pricing database 142. If block 912 identifies a lower-cost preferred drug that is a therapeutic alternate, then processing proceeds with block 914 identifying the therapeutic alternate product name, quantity and price. Processing then proceeds to block 916. Likewise, processing also proceeds to block 916 if there is no lower-cost preferred brand drug identified in block 912.

In block 916, the alternate price qualification module 106 may determine whether the U&C price exceeds the generic drug price for the generic drug identified as the therapeutic alternate in the alternate pricing database 142. For example, in block 916, the generic drug that is the therapeutic alternate may be identified by matching the therapeutic category of the requested drug with the therapeutic category of the generic drug in the alternate pricing database 142. If block 916 identifies a lower-cost preferred drug that is a therapeutic alternate, then processing proceeds with block 918 identifying the therapeutic alternate product name, quantity and price. Processing then proceeds to block 920 determining whether any lower-cost therapeutic alternates were identified in blocks 914 and 918. If there were any identified lower-cost therapeutic alternates identified in blocks 914 and 918, then processing continues to block 922. According to block 922, the alternate price qualification module 106 may report the lower-cost therapeutic alternates, including the product name, quantity, and price, to the switch provider 104, which may notify the pharmacy 102 of such lower-cost therapeutic alternates. On the other hand, if there were no identified lower-cost therapeutic alternates identified in blocks 914 and 918, then the alternate pricing qualification module 106 may exit, and the switch provider 104 may optionally be notified that no lower-cost therapeutic alternate is available, as illustrated in block 910.

It will be appreciated that many variations of the above-described embodiments of the invention are available. For example, according to an example embodiment of the invention, the alternate pricing qualification module such as alternate pricing qualification module 106 in FIG. 1 may be accessible utilizing a variety of remote devices. According to an example embodiment of the invention, these remote devices may include one or more personal computers (e.g., Internet-based computers), kiosks, and the like that are operative to communicate with the alternate pricing qualification module 106. According to an alternate embodiment of the invention, a personal computer may access the alternate pricing qualification module 106 by accessing a webpage via an Internet browser. A user (e.g., patient) of the webpage may enter a drug identification, a quantity of the drug, a price of the drug, and/or a pharmacy identification into one or more fields of the webpage. The webpage may then provide the entered information to the alternate pricing qualification module 106. The alternate pricing qualification module 106 may then query the alternate pricing database 142 to determine whether there are any lower-cost therapeutic alternates, including preferred brand drugs or preferred generic drugs. If there are any lower-cost therapeutic alternates available, then the alternate pricing qualification module 106 may present these therapeutic alternates to the user's webpage.

Similarly, a kiosk at a pharmacy location or other healthcare location may include a dedicated program or Internet browser for accessing the alternate pricing qualification module 106, according to another example embodiment of the invention. The user at the kiosk may then enter a drug identification, a quantity of the drug, a price of the drug, and/or a pharmacy identification into the dedicated program or Internet browser, and the entered information may be provided to the alternate pricing qualification module 106. The alternate pricing qualification module 106 may then query the alternate pricing database 142 to determine whether there are any lower-cost therapeutic alternates, including preferred brand drugs or preferred generic drugs. If there are any lower-cost therapeutic alternates available, then the alternate pricing qualification module 106 may present these therapeutic alternates to the user of the kiosk.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method for alternate pricing, comprising:
receiving, from a pharmacy computer, first information associated with a first claim transaction, wherein the first information identifies a first drug, a first quantity of the first drug, and a first price for the first drug;
determining a first product classification for the identified first drug, wherein the first product classification indicates that the identified first drug is a preferred drug;
automatically updating an alternate pricing database with the first price for the first drug based at least in part on determining that the first price for the first drug does not exceed a previously stored price for the first drug in the alternate pricing database;
receiving, from a pharmacy computer, a second claim request, wherein the second claim request identifies a requested drug and a price for the requested drug, and further specifies a claims processing system as a destination of the second claim request;
identifying the first drug as a therapeutic alternative for the requested drug;
determining, based upon the first price for the first drug in the updated alternate pricing database, that the first drug is available at a lower cost than the requested drug;
determining a denial of the second claim request based upon the determination that the first drug is available at the lower cost than the requested drug; and transmitting, to the pharmacy computer that sent the second claim request, a response to the second claim request, the response indicating the denial of the second claim request and further including an indication of availability of the first drug as the therapeutic alternative and pricing information associated with the first drug, and associated with the denial of the second claim request response, the second claim request is not delivered to its intended destination, the claims processing system;

wherein the prior steps are performed by a provider computer.

2. The method of claim 1, wherein identifying the first drug as the therapeutic alternative for the requested drug includes:
   determining a therapeutic category for the requested drug, and
   identifying one or more alternate drugs, including the first drug, in an alternate pricing database that are associated with the determined therapeutic category,
   wherein the prior steps are performed by one or more provider computers.

3. The method of claim 2, wherein the alternate pricing database is dynamically updated based upon claim transactions between one or more pharmacy computers and one or more payor computers.

4. The method of claim 1, wherein prior to updating the alternate pricing database, the method further includes:
   determining that the first quantity of the first drug is a standard quantity; or
   determining that the received first price is within a predetermined amount or predetermined percentage from an industry-established cost base of the first drug,
   wherein the prior steps are performed by one or more provider computers.

5. The method of claim 1, wherein the first product classification indicates that the identified first drug is a preferred brand drug or a preferred generic drug.

6. The method of claim 1, further comprising:
   receiving second information associated with a second claim transaction, wherein the second information identifies a second drug, a second quantity of the second drug, and a second price for the second drug,
   determining that the second drug is a non-preferred drug or the second quantity is a non-standard quantity; and
   based upon the determining that the second drug is the non-preferred drug or the second quantity is the non-standard quantity, the alternate database is not updated with the second price for the second drug,
   wherein the prior steps are performed by one or more provider computers.

7. The method of claim 1, wherein the second response further includes an override code, wherein the override code allows the pharmacy computer to resubmit the second claim request for adjudication by a payor.

8. The method of claim 1, wherein the first price for the first drug is a Usual and Customary (U&C) price for the first drug.

9. The method of claim 1, wherein the second claim request further includes a second quantity of the requested drug, and further comprising:
   determining that the second quantity of the requested drug is a standard quantity before identifying the first drug as the therapeutic alternative for the requested drug,
   wherein the prior step is performed by one or more provider computers.

10. The method of claim 1, wherein the second claim request is associated with a customer of a pharmacy associated with the pharmacy computer.

11. A system comprising:
   a switch provider computer that interconnects a pharmacy computer and a payor computer, wherein the switch provider computer is operative to route a first claim transaction between the pharmacy computer and the payor computer; and
   an alternate pricing qualification module in communication with the switch provider computer, the alternate pricing qualification module being implemented as computer-executable instructions of the switch provider computer or another computer in communication with the switch provider computer, wherein the alternate pricing qualification module is executed by the switch provider computer or another computer to:
      receive, from the pharmacy computer, first information associated with the first claim transaction, wherein the first information identifies a first drug, a first quantity of the first drug, and a first price for the first drug;
      determine a first product classification for the identified first drug, wherein the first product classification indicates that the identified first drug is a preferred drug;
      automatically update an alternate pricing database with the first price for the first drug based at least in part on determining that the first price for the first drug does not exceed a previously stored price for the first drug in the alternate pricing database;
      receive, from a pharmacy computer, a second claim request, wherein the second claim request identifies a requested drug and a price for the requested drug;
      identify the first drug as a therapeutic alternative for the requested drug;
      determine, based upon the first price for the first drug in the updated alternate pricing database, that the first drug is available at a lower cost than the requested drug;
      determine a denial of the second claim request based upon the determination that the first drug is available at the lower cost than the requested drug; and
      transmit, to the pharmacy computer that sent the second claim request, a response to the second claim request, the response indicating the denial of the second claim request and further including an indication of availability of the first drug as the therapeutic alternative and pricing information associated with the first drug, and associated with the denial of the second claim request response, the second claim request is not delivered to its intended destination, the claims processing system.

12. The system of claim 11, wherein the first drug is identified as the therapeutic alternative for the requested drug by:
   determining a therapeutic category for the requested drug, and
   identifying one or more alternate drugs, including the first drug, in an alternate pricing database that are associated with the determined therapeutic category.

13. The system of claim 12, wherein the alternate pricing database is dynamically updated based upon claim transactions between one or more pharmacy computers and one or more payor computers.

14. The system of claim 11, wherein prior to updating the alternate pricing database, the alternate pricing qualification module is further executed by the switch provider computer or another computer to:
   determine that the first quantity of the first drug is a standard quantity, or determine that the received first price is within a predetermined amount or percentage from an industry-established cost base of the first drug.

15. The system of claim 11, wherein the first product classification indicates that the identified first drug is a preferred brand drug or a preferred generic drug.

16. The system of claim 11, wherein the switch provider computer is further operative to route a second claim transaction between the pharmacy computer and the payor computer, wherein the alternate price qualification module is operative to:

receive second information associated with the second claim transaction from the pharmacy, wherein the second information identifies a second drug, a second quantity of the second drug, and a second price for the second drug, determine that the second drug is a non-preferred drug or the second quantity is a non-standard quantity, based upon the determination that the second drug is the non-preferred drug or the second quantity is the non-standard quantity, the alternate database is not updated with the second price for the second drug.

17. The system of claim 11, wherein the second response further includes an override code, wherein the override code allows the pharmacy computer to resubmit the second claim request for adjudication by a payor.

18. The system of claim 11, wherein the first price for the first drug is a Usual and Customary (U&C) price for the first drug.

19. The system of claim 11, wherein the second claim request further includes a second quantity of the requested drug, and wherein the alternate pricing qualification module is operative to:

determine that the second quantity of the requested drug is a standard quantity before identifying the first drug as the therapeutic alternative for the requested drug.

20. The system of claim 11, wherein the second claim request is associated with a customer of a pharmacy associated with the pharmacy computer.

* * * * *